(12) United States Patent
Winter et al.

(10) Patent No.: US 11,439,386 B2
(45) Date of Patent: Sep. 13, 2022

(54) INTERLOCKING TWO-PART SEWING NEEDLE FOR DOUBLE LOOP STITCHING

(71) Applicant: Winter Innovations, Inc., Knoxville, TN (US)

(72) Inventors: Lia Lynn Winter, Pittsburgh, PA (US); Preston Dishner, Piney Flats, TN (US); Ted Vermette, Brewerton, NY (US)

(73) Assignee: Winter Innovations, Inc., Knoxville, TN (US)

(*) Notice: Subject to any disclaimer, the term of this patent is extended or adjusted under 35 U.S.C. 154(b) by 0 days.

(21) Appl. No.: 17/534,001

(22) Filed: Nov. 23, 2021

(65) Prior Publication Data
US 2022/0081817 A1 Mar. 17, 2022

Related U.S. Application Data

(63) Continuation-in-part of application No. 16/537,088, filed on Aug. 9, 2019, now Pat. No. 11,213,290, which is a continuation-in-part of application No. 16/151,591, filed on Oct. 4, 2018, now Pat. No. 10,792,036.

(60) Provisional application No. 62/586,690, filed on Nov. 15, 2017.

(51) Int. Cl.
*A61B 17/06* (2006.01)

(52) U.S. Cl.
CPC .... *A61B 17/06* (2013.01); *A61B 2017/06057* (2013.01)

(58) Field of Classification Search
CPC ... A61B 17/04; A61B 17/06; A61B 17/06004; A61B 17/06066; A61B 2017/06052; A61B 2017/06019; A61B 2017/06028; A61B 2017/06057; A61B 2017/061; D05B 85/10
See application file for complete search history.

(56) References Cited

U.S. PATENT DOCUMENTS

| | | | |
|---|---|---|---|
| 2008/0051833 A1* | 2/2008 | Gramuglia | A61B 17/06128 606/222 |
| 2015/0164500 A1* | 6/2015 | Gordon | A61B 17/0482 606/148 |

* cited by examiner

*Primary Examiner* — Melanie R Tyson
(74) *Attorney, Agent, or Firm* — Chambliss, Bahner & Stophel, P.C.; Stephen D. Adams (57) ABSTRACT

An interlocking two-part sewing needle includes a first needle portion having a needle tip and a second needle portion configured to be inserted into the first needle portion for removably connecting the first needle portion and the second needle portion together. A needle receiver is formed in the first needle portion and is configured to receive the second needle portion when the second needle portion is inserted into the first needle portion. The needle receiver includes one or more non-resistance sections. Each non-resistance section is configured to exert only a friction force on the second needle portion when the second needle portion is inserted into the needle receiver. Additionally, the needle receiver includes one or more resistance sections. Each resistance section is configured to exert a compressive force on the second needle portion when the second needle portion is inserted into the needle receiver.

20 Claims, 6 Drawing Sheets

INTERLOCKING TWO-PART SEWING NEEDLE FOR DOUBLE LOOP STITCHING

CROSS-REFERENCE TO RELATED APPLICATIONS

This application is a continuation-in-part of application Ser. No. 16/537,088, filed Aug. 9, 2019, which is a continuation-in-part of application Ser. No. 16/151,591, filed Oct. 4, 2018, now U.S. Pat. No. 10,792,036, which claims priority to U.S. Provisional Patent Application No. 62/586,690, filed on Nov. 15, 2017, each of the foregoing applications entitled METHODS AND SYSTEMS FOR DOUBLE LOOP STITCHING; the entire contents of all of the foregoing applications being incorporated herein by reference.

FIELD OF THE INVENTION

This invention generally relates to a method and apparatus for stitching. More specifically, the present invention, relates to an interlocking two-part sewing needle including a first needle portion having an integrated needle receiver for guiding the insertion of a second needle portion into engagement with the first needle portion and a needle portion interlock for removably connecting the first needle portion and the second needle portion together.

BACKGROUND OF THE INVENTION

Ligament replacement or repair is very common amongst athletes and active individuals. In a typical ligament replacement surgery, the torn ligament is replaced by soft tissue graft, which may be taken from the patient's own body or from a donor. During the surgery, the surgeon uses a needle and heavy-duty, non-degradable suture to reinforce the ends of the graft. The reinforced graft is then implanted into the knee and affixed so that it serves the same anatomical function that the torn ligament served prior to the injury.

The conventional graft preparation process discussed above may be improved through use of the two-part needle and methods that are detailed in U.S. Pat. No. 10,792,036 and application Ser. No. 16/537,088, the contents of which are hereby incorporated by reference in their entirety. That two-part needle and the related methods may be further improved by a two-part needle and method of use that provides for a more secure connection between the two needle portions.

Notes on Construction

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless specified herein or clearly indicated by context. The term "operatively connected" is such an attachment, coupling or connection that allows the pertinent structures to operate as intended by virtue of that relationship.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

The apparatus and method disclosed herein may be used for traditional sewing processes, such as joining fabric or textiles in the production of clothing, etc., in surgical procedures, and other similar processes. As such, in the description that follows, the term "thread" is used broadly and interchangeably to refer to textile-type strands used in traditional sewing processes, to refer to medical sutures or other similar materials for use in performing surgery, and the like. Similarly, the term "sewing" is used broadly to refer to the traditional sewing type processes or surgical procedures that use needle and thread. Lastly, the term "sewing material" is used broadly to refer to textile or other types of materials used in traditional sewing type processes or to graft and other similar materials used in surgical procedures, such as ligaments, tendons, or other soft tissue.

Additionally, the apparatus and method disclosed herein may be used in removably connecting together elongate structures. Unless specifically noted otherwise, the term "elongate structure" should be interpreted broadly to refer to any type of tube, cylinder, cannula, conduit, chute, duct, etc. that can be crimped or that can otherwise be provided with one or more crimped sections. These elongate structures may be used inside of the medical field and also outside of the medical field. As one example of a use outside of the medical field, tube-shaped jump rope handles may be removably connected together using the apparatus and method of the present invention.

SUMMARY OF THE INVENTION

The above and other needs are met by an interlocking two-part sewing needle that includes a first needle portion having a needle tip and a second needle portion configured to be inserted into the first needle portion for removably connecting the first needle portion and the second needle portion together. A needle receiver is formed in the first needle portion and is configured to receive the second needle portion when the second needle portion is inserted into the first needle portion. The needle receiver includes one or more non-resistance sections. Each non-resistance section is configured to exert only a friction force on the second needle portion when the second needle portion is inserted into the needle receiver. Additionally, the needle receiver includes one or more resistance sections. Each resistance section is configured to exert a compressive force on the second needle portion when the second needle portion is inserted into the needle receiver.

In certain embodiments, the needle receiver includes a channel that, when the second needle portion is inserted into the first needle portion, partially surrounds the second needle portion. The channel is formed by a bottom that is located between a pair of shoulders that are separated from one another by a first space. In some cases, one or more resistance sections is located in the channel. Further, in some cases, a non-resistance sections is also located in the channel.

In certain cases, the resistance sections include a channel crimp that is formed by a portion of the shoulders of the channel that are separated from one another by a second space that is less than the first space. The second space is sized such that the portion of the shoulders at the channel crimp exert the compressive force on the second needle when the first needle portion and the second needle portion are connected together. In some embodiments, the non-resistance sections may include a portion of the shoulders located at the channel but not located at the channel crimp that exerts only a friction force on the second needle portion when the first needle portion and the second needle portion are connected together.

In certain embodiments, the needle receiver includes a bore that is formed and extends longitudinally within the first needle portion. In such cases, the first needle portion and the second needle portion are connected together by sliding the second needle into the bore such that the bore substantially surrounds at least a portion of the second needle portion. In some cases, a resistance section is located in the bore. In some cases, a non-resistance section is also located in the bore. In some embodiments, the first resistance section is sized and configured to arrest sliding movement of the second needle portion with respect to the first needle portion.

Certain embodiments of the invention include a stop crimp that is formed in the first needle portion that reduces a widest internal wall-to-wall size of the bore taken at a cross section. As a result, when the first needle portion and the second needle portion are connected together, the second needle portion contacts the stop crimp within the bore and the stop crimp exerts the compressive force on the second needle portion. Certain embodiments of the invention include a stop crimp receiver, which is provided in the second needle portion. In those cases, when the first needle portion and the second needle portion are connected together, the stop crimp is configured to snap into the stop crimp receiver for removably connect the first needle portion and the second needle portion together.

In certain embodiments of the invention, the resistance section includes a first resistance section that is configured to exert a first compressive force on the second needle portion and a second and separate resistance section that is configured to exert a second compressive force on a different and longitudinally spaced apart portion of the second needle portion. In certain embodiments of the invention, at least one of the first needle portion and the second needle portion is formed from a hollow tube. In certain cases, one end of a thread is connected to a trailing end of the first needle portion and an opposing end of the thread is connected to a trailing end of the second needle portion. In certain embodiments of the invention, the compressive force is greater than the friction force exerted on the second needle portion.

Also disclosed herein is an interlocking two-part sewing needle that includes a first needle portion formed from a hollow tube with an internal bore that extends from a leading end of the first needle portion to a trailing end of the first needle portion to provide open ends. The sewing needle also includes a channel that is located at the trailing end of the first needle portion. The channel includes a bottom located between a pair of shoulders that are separated from one another by a first space. A needle tip is provided at the leading end of the first needle portion. The two-part sewing needle also includes a second needle portion that is configured to be removably connected together with the first needle portion by inserting a leading end of the second needle portion into the internal bore via the trailing end of the first needle portion and then sliding the second needle portion at least partially through the internal bore. A channel crimp is provided in a portion of the channel. A portion of the shoulders located at the channel crimp are separated by a second space that is smaller than the first space. As a result, the shoulders contact the second needle portion at the channel crimp and align the second needle portion with the internal bore. The two-part needle also includes a stop crimp that constricts the bore and exerts a compressive force on the second needle portion for resisting movement of the second needle portion through the bore beyond the stop crimp.

Also disclosed herein is a method of using a needle. The method requires the step of providing a two-part sewing needle that includes a first needle portion having a needle tip, a second needle portion configured to be inserted into the first needle portion for removably connecting the first needle portion and the second needle portion together, and a needle receiver formed in the first needle portion that is configured to receive the second needle portion when the second needle portion is inserted into the first needle portion. The needle receiver includes one or more non-resistance sections that are each configured to exert only a friction force on the second needle portion when the second needle portion is inserted into the needle receiver. Additionally the needle receiver also includes one or more resistance sections that are each configured to exert a compressive force on the second needle portion when the second needle portion is inserted into the needle receiver. The method further requires the step of removably connecting the first needle portion and the second needle portion together by inserting the second needle portion into the needle receiver such that a friction force is exerted onto the second needle portion by one of the one or more non-resistance sections. Finally, the method requires the step of, with one of the one or more resistance sections, exerting a first compressive force on the second needle portion that is greater than the friction force exerted on the second needle portion.

In certain embodiments, the method also includes the step of, with another one of the one or more resistance sections, exerting a second compressive force on a different and longitudinally spaced apart portion of the second needle portion that is greater than the first compressive force and greater than the friction force.

In certain embodiments, the first compressive force is provided by a channel crimp formed in a portion of the channel, where a portion of the shoulders located at the channel crimp is separated by a second space that is smaller than the first space such that the shoulders contact the second needle portion at the channel crimp and exert the first compressive force on the second needle portion and aligns the second needle portion with the bore. Additionally, the second compressive force is provided by a stop crimp that constricts the bore and exerts the second compressive force on the second needle portion and resists movement of the second needle portion through the bore beyond the stop crimp.

Lastly, the present disclosure also provides a method for removably connecting together elongate structures that includes the step of providing a first elongate structure having a longitudinal axis, a leading end, a trailing end, and an elongate receiver having an opening formed at the trailing end of the elongate structure and extending along the longitudinal axis. Additionally, the method includes the step of providing a second elongate structure having a longitudinal axis, a leading end, and a trailing end. Next, the leading end of the second elongate structure is inserted into the opening of the elongate receiver of the first elongate structure such that the longitudinal axes of the first and second elongate structures are parallel. Then, the method includes the step of sliding the second elongate structure into the elongate receiver. A non-resistance section is provided in the elongate receiver of the first elongate structure. With the non-resistance section, only a friction force is exerted on the second elongate structure as the second elongate structure is sliding into the elongate receiver. The method also includes the step of providing a resistance section in the elongate receiver of the first elongate structure. With the resistance section, a compression force is exerted on the second elongate structure as the second elongate structure is inserted into the elongate receiver.

In certain embodiments, the first elongate structure includes a hollow tube having an internal bore formed by an outer wall providing opposing open ends. Additionally, the resistance section includes a crimp formed in the outer wall of the hollow tube that reduces a widest internal wall-to-wall spacing of the internal bore located at the crimp and taken at a cross section. Lastly, the second elongate structure has a width that is greater than the widest internal wall-to-wall spacing. The method further includes the step of exerting a compressive force onto the second elongate structure by contacting the second elongate structure with an internal wall surface located at the crimp. In certain cases, the second elongate structure includes an outer wall and a crimp receiver formed in the outer wall and the method further includes the step of positively engaging a portion of the outer wall located at the crimp into the crimp receiver. In certain embodiments, the first and second elongate structures each include a hollow tube, each having an internal bore formed by an outer wall providing opposing open ends.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED
EMBODIMENTS OF THE INVENTION

This description of the preferred embodiments of the invention is intended to be read in connection with the accompanying drawings, which are to be considered part of the entire written description of this invention. The drawings are not necessarily to scale, and certain features of the invention may be shown exaggerated in scale or in somewhat schematic form in the interest of clarity and conciseness.

Figure 1:
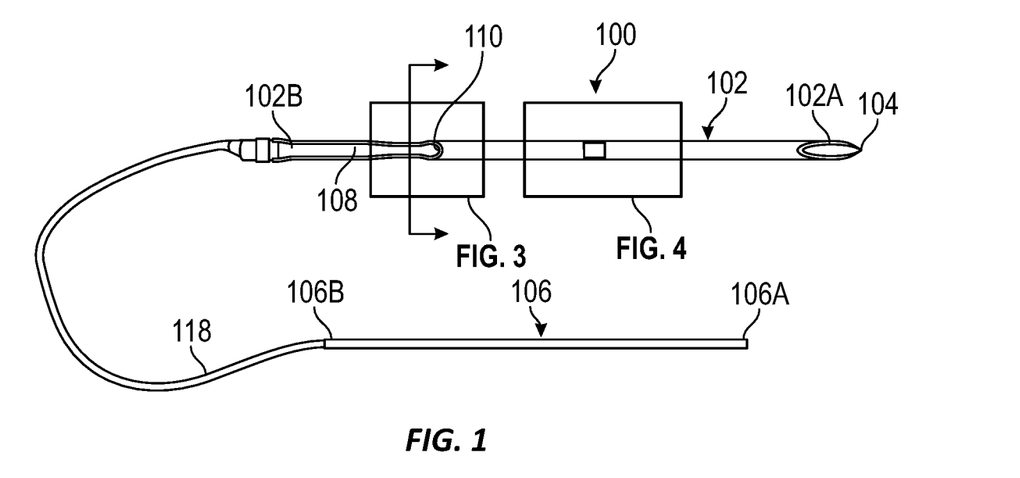
FIG. 1 is a plan view depicting a crimped two-part needle according to an embodiment of the present invention, where first and second needle portions, which are connected together by a suture/thread, are shown in a separated configuration.
Figure 2:
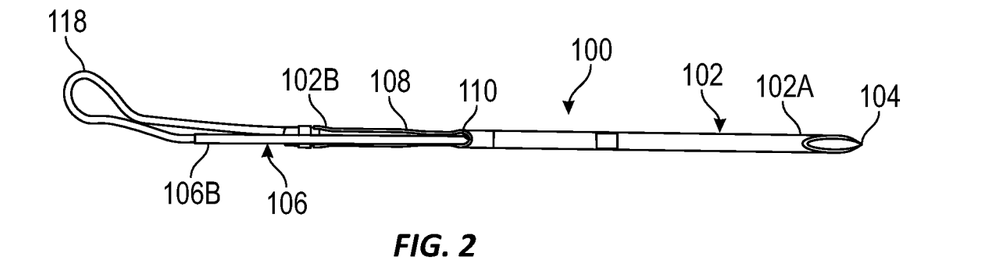
FIG. 2 is a plan view depicting the needle of FIG. 1, where the first needle portion and the second needle portion are shown in a connected and locked together configuration.
Figure 5:
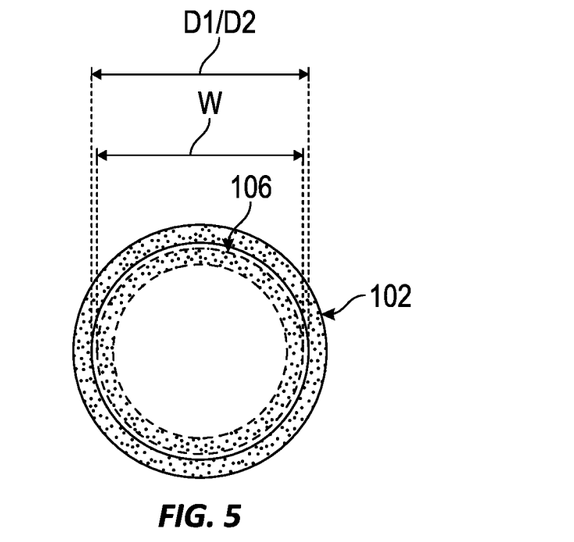
FIG. 5 is a cross sectional view showing a cross section of the first needle portion and the second needle portion of FIG. 3.

With initial reference to FIGS. 1, 2, and 5 there is provided an interlocking two-part sewing needle 100 according to an embodiment of the present invention. The needle 100 includes a first needle portion 102 having a leading end 102A, a trailing end 102B, and a needle tip 104 located at the leading end; and a second needle portion 106 having a leading end 106A and a trailing end 106B. In certain embodiments, the first needle portion 102 is a hollow tube. In certain other embodiments, including the illustrated embodiment, both the first needle portion and the second needle portion 102, 106 are formed from hollow tubes. The second needle portion 106 is configured to be inserted into the first needle portion 102 in order to removably connect the first needle portion and the second needle portion together during the sewing process (e.g., prior or during a ligament replacement surgery). The needle 100 may also include a thread 118 (e.g., a suture), wherein one end of the thread is connected to the trailing end 102B of the first needle portion 102 and an opposing end of the thread is connected to a trailing end 106B of the second needle portion 106. This combined needle 100 and thread 118 may be used according to the methods described in U.S. Pat. No. 10,792,036 and application Ser. No. 16/537,088.

A needle receiver 108 is formed in the first needle portion 102 and is configured to receive the second needle portion 106 when the first needle portion and the second needle portion are connected together. The second needle portion 106 may also be selectively removed from the needle receiver 108 when the first needle portion and the second needle portion 102, 106 are separated from one another. The second needle portion 106 may be inserted into and removed from any portion of the first needle portion 102. For example, in certain embodiments, the needle receiver 108 may include a slot or indentation (not shown) formed in the outside of the side wall of the first needle portion 102. The slot is preferably sized and configured to allow the second needle portion 106 to be inserted and, preferably, removably attached to the first needle portion 102, such as by clips or other similar retention means integrated into the slot.

However, in preferred embodiments, the second needle portion 106 is inserted longitudinally into an opening formed in the first needle portion 102. As mentioned above, the first needle portion and the second needle portion 102, 106 are formed from hollow tubes, such that openings are located at each end of both needle portions 102, 106. These tubes each include a bore 110 that extends longitudinally through the tube and that forms part of the needle receiver 108. The bore has an opening having a first space D1 (i.e., the internal diameter or the widest internal wall-to-wall spacing separating taken at a cross section).

In other embodiments, the bore 110 extends only partially through the needle portions 102, 106, such that only one end is provided with an opening. In preferred embodiments, the bore 110 of the first needle portion 102 is sized and configured such that the second needle portion 106 may be partially or fully inserted into the bore. As more fully described below, when the second needle portion 106 is inserted into the first needle portion 102, the bore 110 of the first needle portion "substantially" surrounds the inserted portion of the second needle portion.

Figure 3:
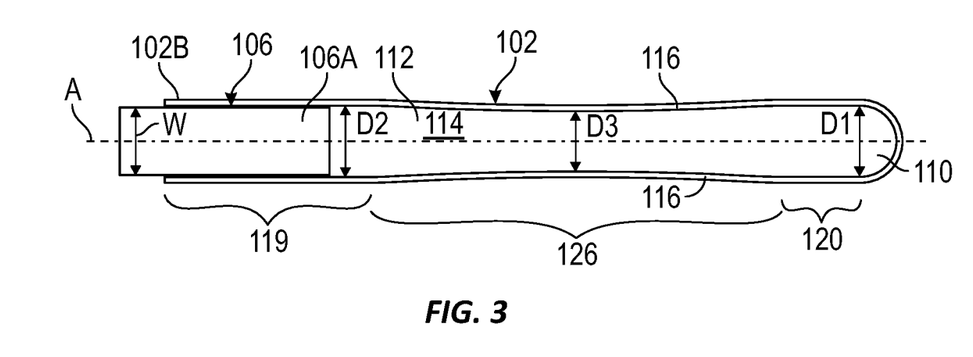
FIG. 3 is a plan view depicting a first resistance section of the first needle portion of FIG. 1 that is enclosed by a box indicated by "FIG. 3"
Figure 6A:
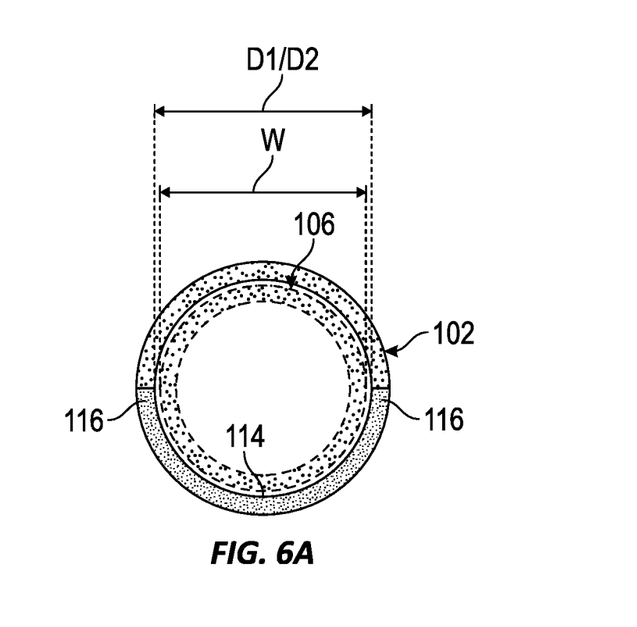
FIG. 6A is a cross sectional view showing a cross section of the first needle portion and the second needle portion of FIG. 3 and also a cross section of a channel shown in FIG. 3.

Next, the portion of the needle 100 shown in FIG. 1 that is enclosed by a box labeled "FIG. 3" is shown and enlarged in FIG. 3. In FIG. 3, the leading end 106A of the second needle portion 106 is engaged with a portion of the trailing end 102B of the first needle portion 102. In particular, in preferred embodiments, the needle receiver 108 also includes a channel 112 that is located at the trailing end 102B of the first needle portion and is configured to receive the second needle portion 106, as shown in FIG. 3. With continued reference to FIG. 3 and with further reference to FIG. 6A, the channel 112 is formed by a bottom 114 located between a pair of shoulders 116 that are preferably separated from one another by a second space D2 (i.e., the widest internal wall-to-wall spacing separating taken at a cross section), which may be equal to space D1. However, depending on the size of the shoulders 116, the spacing between the shoulders may be more or less than space D1. The channel 112 is sized and configured to receive and to "partially" surround the second needle portion 106 when the second needle portion is connected together with the first needle portion 102.

When "partially" surrounded by just the shoulders 116, the second needle portion 106 is not secured within the channel 112. Instead, the second needle portion 106 may be easily inserted and removed (i.e., lifted) from the channel 112 without resistance. In other words, there is sufficient space between the shoulders 116 (i.e. space D2) to enable the second needle portion 106 to pass through easily and without resistance. By contrast, when a portion of the second needle portion 106 is inserted into the bore 110 and that inserted portion is "substantially" surrounded by the bore, the inserted portion of the second needle portion is secured within the bore and cannot be removed (i.e., lifted out of the bore) without resistance. In certain cases, the bore 110 fully surrounds the inserted portion of the second needle portion 106. In other cases, there may be a small slot or opening, similar to the space D2 between the shoulders 116. However, that slot or opening provides an insufficient amount of space to allow the inserted portion of the second needle portion 106 to pass through easily or without resistance.

The channel 112 may be formed by removing a portion of the wall that forms the bore 110. Alternatively, the channel 112 may be attached to the end of the bore 110. In either case, the channel 112 is preferably connected continuously with the bore 110 such that the second needle portion 106 can move easily between the bore and channel as it is inserted into and removed from the first needle portion 102.

As the first needle portion and the second needle portion 102, 106 are engaged with one another (i.e., as the second needle portion is inserted into the needle receiver 108), they are in sliding contact with one another. As a result of this sliding contact, the needle portions 102, 106 each exert a friction force on the other needle portion. Thus, in preferred embodiments, the needle receiver 108 includes one or more non-resistance sections, where only a friction force is exerted on the second needle portion 106 when the second needle portion interacts with (e.g. is inserted into) the needle receiver of the first needle portion 102. There may be multiple non-resistance sections in various locations of the needle receiver 108, including in the bore 110 and in the channel 112. In FIG. 3, two separate non-resistance sections (the areas generally denoted with reference numbers 119 and 120) are provided, where the second needle portion 106 experiences only a friction force (if contact is made between the needle portions). Now, with reference to FIG. 4, a cutaway view is provided that shows the portion of the needle 100 in FIG. 1 that is surrounded by a box and that is labeled "FIG. 4." In FIG. 4, two additional non-resistance sections (the areas generally denoted with reference numbers 122 and 124) are provided, where the second needle portion 106 experiences only a friction force (again, if contact is made between the needle portions).

Figure 4:
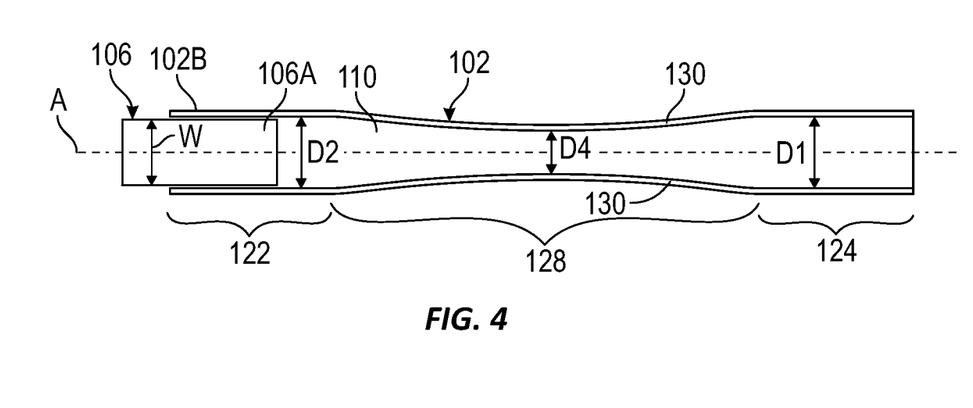
FIG. 4 is a cutaway view depicting the internal structure of a second resistance section of the first needle portion of FIG. 1 that is enclosed by a box indicated by "FIG. 4"

Now, with reference to both FIGS. 3 and 4, the needle 100 also preferably includes one or more resistance sections, where a force that is greater than the above-described friction force is exerted on the second needle portion 106. These one or more resistance sections function as a "needle interlock". As discussed in greater detail below, among other things, the needle interlock, via these resistance sections, assists in guiding the second needle portion 106 as it is joined together with the first needle portion 102. Additionally, the needle interlock provides tactile feedback to help the user to know when the connection between the needle portions 102, 106 is complete. Lastly, the needle interlock assists in maintaining the connection between the needle portions 102, 106.

Unlike the friction force experienced by the second needle portion 106 at the non-resistance sections described above, in preferred embodiments, a compressive force is exerted on the second needle portion by each of the resistance sections. For example, with reference to FIG. 3 and FIG. 6B, a first resistance section is located between non-resistance sections 119 and 120 (i.e., the area generally denoted with reference number 126). In this particular embodiment, the first resistance section is a channel crimp 126 that is formed by a portion of the shoulders 116 of the channel 112. The portion of the shoulders 116 that form the channel crimp 126 are separated from one another by a third space D3 (i.e., the widest internal wall-to-wall spacing separating the shoulders taken at a cross section) that is less than the first space D1. Additionally, the third space D3 is smaller than the widest external width W (i.e., the outer diameter) of the second needle portion 106. The portions of the shoulders 116 that form the channel crimp 126 are configured to flex outwards in order to accommodate the second needle portion 106 (i.e., to allow the second needle portion to be inserted through the channel crimp). As a result, when the second needle portion 106 is inserted into the channel crimp 126, the shoulders 116 flex outwards and the second needle portion is slightly compressed within the channel crimp.

Figure 6B:
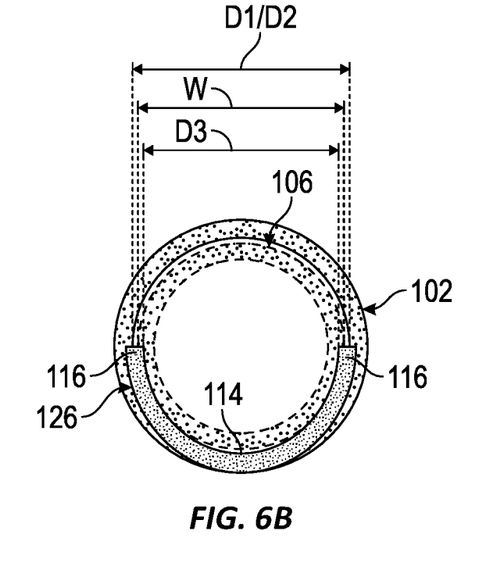
FIG. 6B is a cross sectional view showing a cross section of the first needle portion and the second needle portion of FIG. 3 and also a cross section of a channel crimp shown in FIG. 3.

The channel crimp 126 may be formed by slightly crimping the shoulders 116 of the channel 112 together in order to decrease the distance between them. Other manufacturing methods for providing a section of the channel have a smaller third space D3 than first space D1 may also be used to create the channel crimp 126. The channel crimp 126 may be formed as a narrow crimp in order to compress only a small section of the second needle portion 106. In other cases, as illustrated, a wider and more gradual crimp may be provided in order to compress a wider section of the second needle portion 106.

When in use, the channel crimp 126 initially assists in holding the first needle portion and the second needle portion 102, 106 together as they are being connected. As the leading end 106A and the second needle portion 106 is pushed further into the channel 112, the channel crimp 126 also assists in aligning the second needle portion with the bore 110. More particularly, the channel crimp 126 preferably automatically locates the longitudinal midline of the second needle portion 106 at a center position between the shoulders (i.e., on longitudinal axis A). This enables the second needle portion 106 to pass much more quickly and easily into the bore 110. Since the needle portions 102, 106 are connected and then disconnected from one another multiple times during the course of a surgical procedure, this time reduction can result in significant time and cost savings compared to traditional surgical methods.

Similarly, in preferred embodiments, a second resistance section (the area generally denoted with reference number 128) is located between non-resistance sections 122 and 124. Preferably, the second resistance section is longitudinally spaced apart from the first resistance section. In particular, with continued reference to FIG. 4 and with further reference to FIG. 7, a stop crimp 128 is formed by walls 130 that form the bore 110 and that are separated from one another by a fourth space D4 (i.e., the widest internal wall-to-wall spacing separating the walls). Unlike the shoulders 116, which only partially surrounds the second needle portion 106, the walls 130 that form the bore 110 substantially surround the second needle portion. The stop crimp 128 is created and functions similarly to the channel crimp 126. In particular, the stop crimp 128 may be formed by crimping the walls 130 of the bore 110 together in order to decrease the distance between them. The stop crimp 128 may be formed as a narrow crimp in order to compress only a small section of the second needle portion 106. In other cases, as illustrated, a wider and more gradual crimp may be provided in order to compress a wider section of the second needle portion 106.

Figure 7:
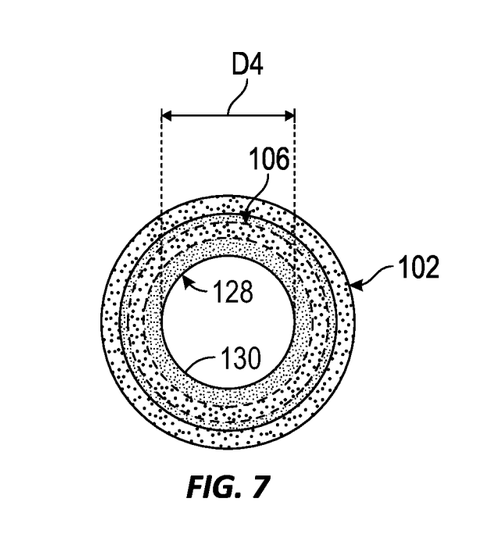
FIG. 7 is a cross sectional view showing a cross section of the first needle portion and the second needle portion of FIG. 4 and also a cross section of a stop crimp shown in FIG. 4.

Like the third space D3, the fourth space D4 is also smaller than the width W of the second needle portion 106. The portions of the walls 130 that form the stop crimp 128 are also configured to flex outwards in order to accommodate a portion the second needle portion 106. However, the stop crimp 128 is configured to exert a greater compressive force on the second needle portion 106 than the channel crimp 126. The stop crimp 128 is configured to constrict the bore 110 and to exert a compressive force on the second needle portion 106 that is different and preferably greater than the compressive force provided by the channel crimp 126, so as to limit or, more preferably, arrest the movement of the second needle portion through the bore and beyond the stop crimp. As a result, in preferred embodiments, the second needle portion 106 may be partially inserted into the stop crimp 126 before coming to a stop as a result of the compression from the stop crimp. This provides a tactile "click" sensation to the user when the second needle portion 106 comes to a stop within the stop crimp 128, which informs the user that the first needle portion 102 and the second needle portion are connected together.

In the descriptions above, the resistance sections 126, 128 are each located between a pair of non-resistance sections 119 and 120 and also 122 and 124, respectively. However, in other embodiments, a pair of resistance sections may be located adjacent one another without a non-resistance section between them. For example, a set of crimps may be provided in the bore 110 that progressively reduce the space within the bore.

Figure 8:
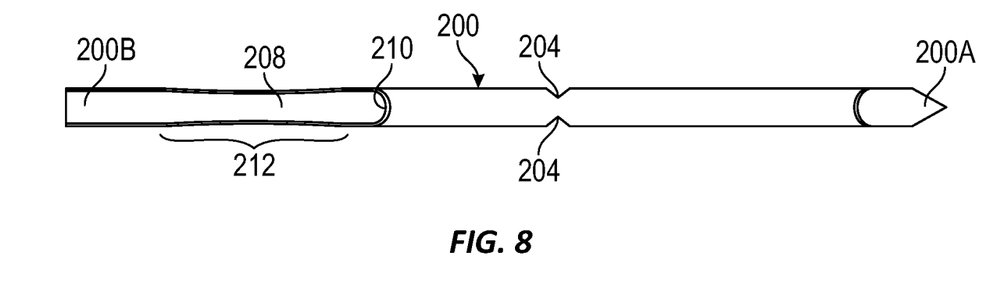
FIG. 8 is a plan view depicting a crimped first needle portion according to an alternative embodiment of the present invention.
Figure 9:
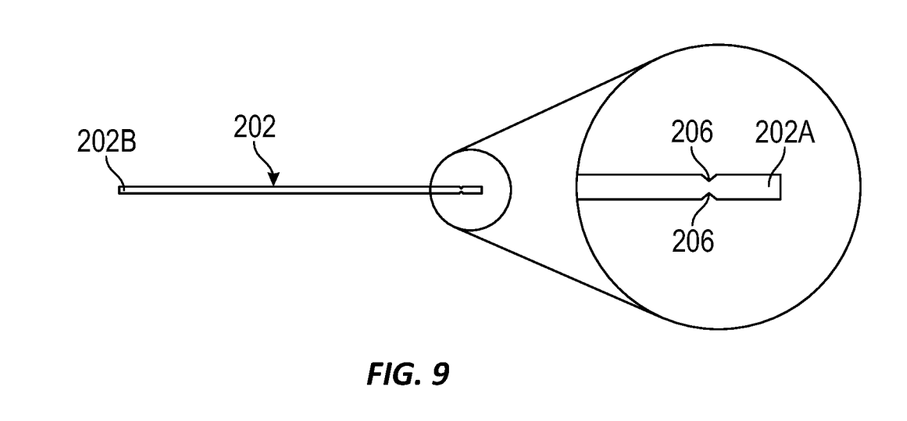
FIG. 9 is detail view depicting a second needle portion having a crimp receiver according to an alternative embodiment of the present invention.
Figure 11:
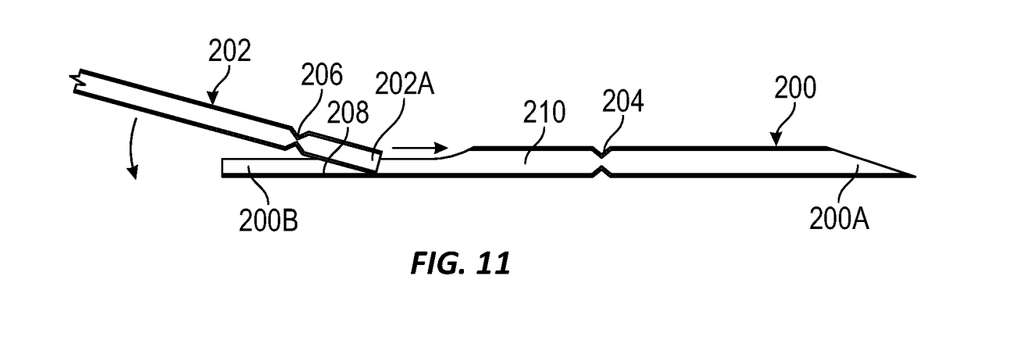
FIG. 11 depicts the first needle portion and the second needle portion of FIG. 10 in the process of being connected together.
Figure 12:
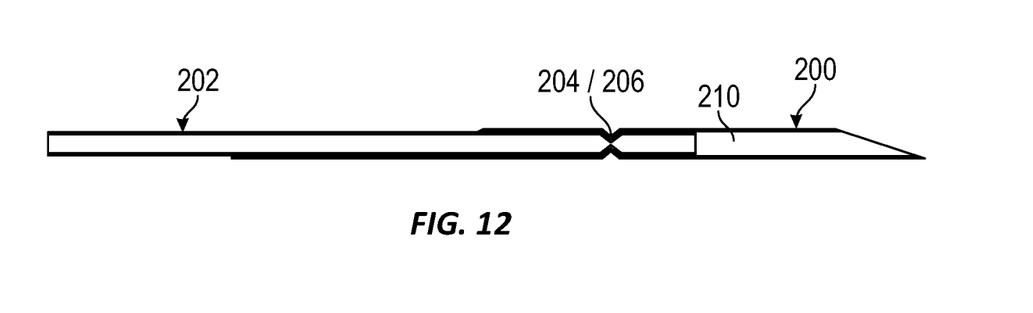
FIG. 12 depicts the first needle portion and the second needle portion of FIG. 10 in a connected and locked together configuration.

Now, with reference to FIGS. 8 and 9, a first needle portion 200 and a second needle portion 202 according to an alternative embodiment of the present invention are shown. First needle portion 200 is structurally and functionally similar to needle portion 102, but includes a shortened stop crimp 204 that is more abrupt or angular than stop crimp 128, which is longer and more gradual in shape. Second needle portion 202 is also structurally and functionally similar to second needle portion 106, but includes a stop crimp receiver 206 near the leading end 202A of the second needle portion (which is located opposite trailing end 202B). The stop receiver 206 is sized and configured to automatically engage with the stop crimp 204 when the second needle portion 202 is placed onto the channel 208 and then inserted into the bore 210 of the first needle portion 200. This process is illustrated in FIGS. 10-12 and is detailed below.

Figure 10:
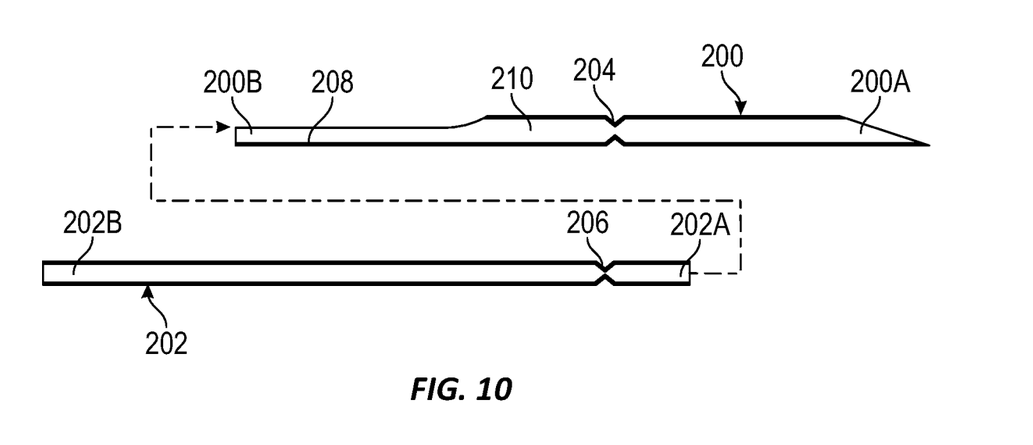
FIG. 10 depicts the first needle portion and the second needle portion of FIGS. 8 and 9 in a separated configuration.

The first needle portion and the second needle portion 200, 202 are initially shown separated from one another (FIG. 10). To connect the needle portions 200, 202 together, the leading end 202A of the second needle portion 202 is inserted into the trailing end 200B of the first needle portion 200 (FIG. 11). The second needle portion 202 then slides forward towards the leading end 200A of the first needle portion, including through the channel 208 and at least a portion of the bore 210. Preferably, this sliding motion is guided by a channel crimp 212 (FIG. 8), as described previously. The second needle portion 202 continues sliding free through the bore 210, guided by the channel crimp, until it reaches the shortened stop crimp 204. At that point, the leading end 202A of the second needle portion 202 contacts the stop crimp 204, which provides resistance to continued forward movement. Pushing the second needle portion 202 through the bore 210 causes the walls of the first needle portion 200 to flex outwards, the walls of the second needle portion 202 to flex inwards, or both, which allows the leading end 202A of the second needle portion to continue sliding beyond the stop crimp 204. The walls of the needle portions 200, 202 remain in flexed state until the stop crimp 204 snaps into engagement with the stop crimp receiver 206 (FIG. 12). This snapping action occurs when the walls of the needle portions 200, 202 return to an unflexed state. Advantageously, the snapping action also provides tactile feedback to the user that the needle portions 200, 202 are removably engaged with one another.

More generally, the present invention provides a method for removably connecting any type of elongate structures together. The method includes the step of first providing a first elongate structure having a longitudinal axis, a leading end, a trailing end, and an elongate receiver having an opening formed at the trailing end of the elongate structure and extending along the longitudinal axis. Next, a second elongate structure having a longitudinal axis, a leading end, and a trailing end is provided. The leading end of the second elongate structure is then inserted into the opening of the receiver of the first elongate structure such that the longitudinal axes of the first and second elongate structures are parallel with one another. Then, the second elongate structure is inserted (e.g., slides) into the elongate receiver of the first elongate structure. The method also requires providing a non-resistance section in the receiver of the first elongate structure, where only a friction force is exerted on the second elongate structure as the second elongate structure is inserted into the needle receiver. Additionally, the method requires providing a resistance section in the receiver of the first elongate structure, where a compression force is exerted on the second elongate structure as the second elongate structure is inserted into the needle receiver.

In certain cases, the first elongate structure is a hollow tube having an internal bore formed by an outer wall. In those cases, the resistance section may include a crimp that is formed in the outer wall of the hollow tube. The crimp reduces the widest internal wall-to-wall spacing of the internal bore located at the crimp taken at a cross section of the internal bore of first elongate structure. Notably, the second elongate structure has a width that is greater than the widest internal wall-to-wall spacing taken at a cross section. As a result, as the second elongate structure is inserted into the receiver of the first elongate structure, a compressive force is exerted onto the second elongate structure by contacting the second elongate structure with an internal wall surface located at the crimp. In certain embodiments, the second elongate structure also includes an outer wall and a crimp receiver formed in the outer wall. As the elongate structures are connected together, the crimp positively engages the crimp receiver in order to provide a removable connection between them. This also provides tactile feedback to the user when the connection has been made. Lastly, in certain cases, both the first and second elongate structures are formed from hollow tubes.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. An interlocking two-part sewing needle comprising:
a first needle portion having a needle tip;
a second needle portion configured to be inserted into the first needle portion for removably connecting the first needle portion and the second needle portion together; and
a needle receiver formed in the first needle portion and configured to receive the second needle portion when the second needle portion is inserted into the first needle portion, the needle receiver including:
one or more non-resistance sections, each configured to exert only a friction force on the second needle portion when the second needle portion is inserted into the needle receiver; and
a needle interlock comprising one or more resistance sections, each configured to exert a compressive force on the second needle portion when the second needle portion is inserted into the needle receiver.

2. The interlocking two-part sewing needle of claim 1 wherein the needle receiver comprises a channel that, when the second needle portion is inserted into the first needle portion, partially surrounds the second needle portion, the channel formed by a bottom located between a pair of shoulders that are separated from one another by a first space.

3. The interlocking two-part sewing needle of claim 2 wherein one of the one or more resistance sections is located in the channel.

4. The interlocking two-part sewing needle of claim 3 wherein one of the one or more non-resistance sections is located in the channel.

5. The interlocking two-part sewing needle of claim 2 wherein one of the one or more resistance sections of the needle interlock comprises a channel crimp formed by a portion of the shoulders of the channel that are separated from one another by a second space that is less than the first space, wherein the second space is sized such that the portion of the shoulders at the channel crimp exert the compressive force on the second needle portion when the first needle portion and the second needle portion are connected together.

6. The interlocking two-part sewing needle of claim 5 wherein one of the one or more non-resistance sections comprises a portion of the shoulders located at the channel but not located at the channel crimp that exerts only a friction force on the second needle portion when the first needle portion and the second needle portion are connected together.

7. The interlocking two-part sewing needle of claim 1 wherein the needle receiver comprises a bore formed and extending longitudinally within the first needle portion such that the first needle portion and the second needle portion are connected together by sliding the second needle portion into the bore such that the bore substantially surrounds at least a portion of the second needle portion.

8. The interlocking two-part sewing needle of claim 7 wherein one of the one or more resistance sections is located in the bore.

9. The interlocking two-part sewing needle of claim 8 wherein one of the one or more non-resistance sections is located in the bore.

10. The interlocking two-part sewing needle of claim 8 wherein the one or more resistance sections is sized and configured to arrest sliding movement of the second needle portion with respect to the first needle portion.

11. The interlocking two-part sewing needle of claim 7 further comprising a stop crimp formed in the first needle portion and reducing a widest internal wall-to-wall size of the bore taken at a cross section such that, when the first needle portion and the second needle portion are connected together, the second needle portion contacts the stop crimp within the bore and the stop crimp exerts the compressive force on the second needle portion.

12. The interlocking two-part sewing needle of claim 11 further comprising a stop crimp receiver provided in the second needle portion, wherein, when the first needle portion and the second needle portion are connected together, the stop crimp is configured to snap into the stop crimp receiver for removably connect the first needle portion and the second needle portion together.

13. The interlocking two-part sewing needle of claim 1 wherein one of the one or more resistance sections is configured to exert a first compressive force on the second needle portion and a second and separate resistance section that is configured to exert a second compressive force on a different and longitudinally spaced apart portion of the second needle portion.

14. The interlocking two-part sewing needle of claim 1 wherein at least one of the first needle portion and the second needle portion is formed from a hollow tube.

15. The interlocking two-part sewing needle of claim 1 further comprising a thread, wherein one end of the thread is connected to a trailing end of the first needle portion and an opposing end of the thread is connected to a trailing end of the second needle portion.

16. The interlocking two-part sewing needle of claim 1 wherein the compressive force is greater than the friction force exerted on the second needle portion at the one or more non-resistance sections.

17. An interlocking two-part sewing needle comprising:
a first needle portion formed from a hollow tube with an internal bore that extends from a leading end of the first needle portion to a trailing end of the first needle portion to provide open ends; a channel located at the trailing end of the first needle portion and including a bottom located between a pair of shoulders that are separated from one another by a first space; and a needle tip provided at the leading end of the first needle portion;
a second needle portion configured to be removably connected together with the first needle portion by inserting a leading end of the second needle portion into the internal bore via the trailing end of the first needle portion and then sliding the second needle portion at least partially through the internal bore;
a channel crimp provided in a portion of the channel wherein a portion of the shoulders located at the channel crimp are separated by a second space that is smaller than the first space such that the shoulders contact the second needle portion at the channel crimp and align the second needle portion with the internal bore; and
a stop crimp that constricts the internal bore and exerts a compressive force on the second needle portion for resisting movement of the second needle portion through the internal bore beyond the stop crimp.

18. A method of using a needle comprising the steps of:
providing a two-part sewing needle comprised by a first needle portion having a needle tip; a second needle portion configured to be inserted into the first needle portion for removably connecting the first needle portion and the second needle portion together; and a needle receiver formed in the first needle portion and configured to receive the second needle portion when the second needle portion is inserted into the first needle portion, the needle receiver including: one or more non-resistance sections, each configured to exert only a friction force on the second needle portion when the second needle portion is inserted into the needle receiver; and a needle interlock having one or more resistance sections, each configured to exert a compressive force on the second needle portion when the second needle portion is inserted into the needle receiver;
removably connecting the first needle portion and the second needle portion together by inserting the second needle portion into the needle receiver such that a friction force is exerted onto the second needle portion by one of the one or more non-resistance sections; and
with one of the one or more resistance sections, exerting a first compressive force on the second needle portion that is greater than the friction force exerted on the second needle portion.

19. The method of claim 18 further comprising the step of, with another one of the one or more resistance sections, exerting a second compressive force on a different and longitudinally spaced apart portion of the second needle portion that is greater than the first compressive force and greater than the friction force.

20. The method of claim 19 wherein:
the needle receiver comprises:
a channel that, when the second needle portion is inserted into the needle receiver, partially surrounds the second needle portion, the channel formed by a bottom located between a pair of shoulders that are separated from one another by a first space;
a bore formed and extending longitudinally within the first needle portion such that the first needle portion and the second needle portion are connected together by sliding the second needle portion into the bore such that the bore substantially surrounds at least a portion of the second needle portion;
the first compressive force is provided by a channel crimp formed in a portion of the channel, wherein a portion of the shoulders located at the channel crimp is separated by a second space that is smaller than the first space such that the shoulders contact the second needle portion at the channel crimp and exert the first compressive force on the second needle portion and aligns the second needle portion with the bore; and
the second compressive force is provided by a stop crimp that constricts the bore and exerts the second compressive force on the second needle portion and resists movement of the second needle portion through the bore beyond the stop crimp.

* * * * *